US012806207B2

(12) United States Patent
Rebouissou et al.

(10) Patent No.: US 12,806,207 B2
(45) Date of Patent: Nov. 24, 2026

(54) COMBINATION OF CISPLATIN AND ELIMUSERTIB FOR THE TREATMENT OF PEDIATRIC LIVER CANCERS

(71) Applicants: INSTITUT NATIONAL DE LA SANTÉ ET DE LA RECHERCHE MÉDICALE, Paris (FR); SORBONNE UNIVERSITÉ, Paris (FR); UNIVERSITÉ PARIS CITÉ, Paris (FR); ASSISTANCE PUBLIQUE-HÔPITAUX DE PARIS (APHP), Paris (FR)

(72) Inventors: Sandra Rebouissou, Paris (FR); Pierre Morel-Ribeiro, Paris (FR); Jean-Charles Nault, Paris (FR); Théo Hirsch, Paris (FR); Jessica Zucman-Rossi, Paris (FR); Jill Pilet, Paris (FR)

(73) Assignees: INSTITUT NATIONAL DE LA SANTÉ ET DE LA RECHERCHE MÉDICALE, Paris (FR); SORBONNE UNIVERSITÉ, Paris (FR); UNIVERSITÉ PARIS CITÉ, Paris (FR); ASSISTANCE PUBLIQUE-HÔPITAUX DE PARIS (APHP), Paris (FR)

( * ) Notice: Subject to any disclaimer, the term of this patent is extended or adjusted under 35 U.S.C. 154(b) by 329 days.

(21) Appl. No.: 18/717,732

(22) PCT Filed: Dec. 20, 2022

(86) PCT No.: PCT/EP2022/086876
§ 371 (c)(1),
(2) Date: Jun. 7, 2024

(87) PCT Pub. No.: WO2023/118062
PCT Pub. Date: Jun. 29, 2023

(65) Prior Publication Data

US 2025/0049807 A1 Feb. 13, 2025

(30) Foreign Application Priority Data

Dec. 21, 2021 (EP) .................................... 21306870

(51) Int. Cl.
*A61K 31/5377* (2006.01)
*A61K 33/243* (2019.01)
*A61P 35/00* (2006.01)

(52) U.S. Cl.
CPC ........ *A61K 31/5377* (2013.01); *A61K 33/243* (2019.01); *A61P 35/00* (2018.01)

(58) Field of Classification Search
CPC .................................................. A61K 31/5377
See application file for complete search history.

(56) References Cited

FOREIGN PATENT DOCUMENTS

WO 2018/153971 A1 8/2018

OTHER PUBLICATIONS

Chavhan et al: "Rare malignant liver tumors in children", Pediatric Radiology, vol. 49, No. 11, p. 1404-1421, Oct. 1, 2019.
Guo et al: "Targeting CDC7 potentiates ATR-CHK1 signaling inhibition through induction of DNA replication stress in liver cancer", Genome Medicine, vol. 13, No. 1, Oct. 18, 2021.
Guo et al: "Additional file 2—Targeting CDC7 potentiates ATR-CHK1 signaling inhibition through induction of DNA replication stress in liver cancer", Genome Medicine, Oct. 18, 2021.
Wengner et al: "The Novel ATR Inhibitor BAY 1895344 Is Efficacious as Monotherapy and Combined with DNA Damage-Inducing or Repair-Compromising Therapies in Preclinical Cancer Models", Molecular Cancer Therapeutics, vol. 19, No. 1, p. 26-38, Oct. 3, 2019.
Wengner et al: "Supplementary tables for: The Novel ATR Inhibitor BAY 1895344 Is Efficacious as Monotherapy and Combined with DNA Damage-Inducing or Repair-Compromising Therapies in Preclinical Cancer Models", Molecular Cancer Therapeutics, Oct. 3, 2019.

*Primary Examiner* — Golam M Shameem
(74) *Attorney, Agent, or Firm* — WCF IP

(57) ABSTRACT

Pediatric liver cancers (PLC) are rare tumors. In particular, hepatoblastomas are usually treated with cisplatin-based neoadjuvant chemotherapy followed by surgical removal of the tumor and adjuvant chemotherapy. However, some hepatoblastomas develop resistance to chemotherapy during the initial neoadjuvant chemotherapy or after tumor recurrence, and the molecular determinants of cisplatin resistance are yet to be discovered. In contrast to hepatoblastomas, pediatric HCCs respond poorly to chemotherapy, and as in adults, they have a poor prognosis if not completely removed by surgery. There is thus an urgent need for new therapeutic strategies to overcome this resistance. Now the inventors demonstrate that Elimusertib and Cisplatin combination shows synergistic efficacy on tumor cell viability inhibition in pediatric liver cancer cell lines. The present invention thus relates to the combination of cisplatin and Elimusertib for the treatment of pediatric liver cancers.

9 Claims, 10 Drawing Sheets

Figure 1:
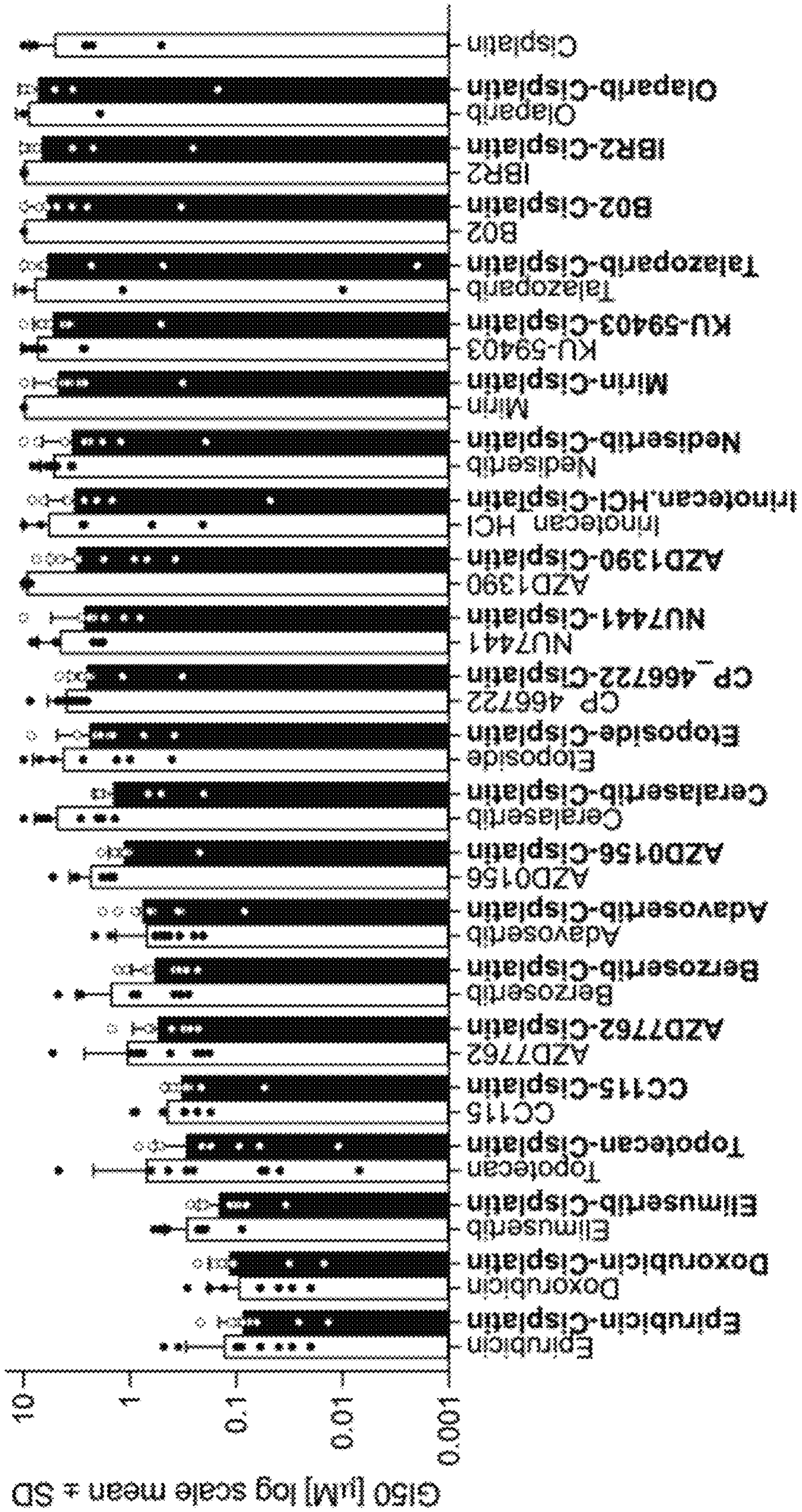

COMBINATION OF CISPLATIN AND ELIMUSERTIB FOR THE TREATMENT OF PEDIATRIC LIVER CANCERS

FIELD OF THE INVENTION

The present invention is in the field of medicine, in particular oncology.

BACKGROUND OF THE INVENTION

Pediatric liver cancers (PLC) are rare tumors and therefore have not been molecularly characterized in large series. Hepatoblastomas represent about 67% to 80% of all PLCs worldwide, generally developing before five years of age on nonfibrotic liver. Hepatoblastomas are characterized by their histologic heterogeneity, with three main histology patterns—fetal, embryonal, and mesenchymal—that often coexist within a single tumor. Hepatoblastomas are usually treated with cisplatin-based neoadjuvant chemotherapy and followed by surgical removal of the tumor and adjuvant chemotherapy, leading to >80% five-year survival (López-Terrada D, Alaggio R, de Dávila MT, Czauderna P, Hiyama E, Katzenstein H, et al. *Towards an international pediatric liver tumor consensus classification: proceedings of the Los Angeles COG liver tumors symposium. Mod Pathol* 2014; 27:472-91). However, some hepatoblastomas develop resistance to chemotherapy during the initial neoadjuvant chemotherapy or after tumor recurrence, and the molecular determinants of cisplatin resistance are yet to be discovered. In contrast to hepatoblastomas, pediatric HCCs respond poorly to chemotherapy, and as in adults, they have a poor prognosis if not completely removed by surgery. There is thus an urgent need for new therapeutic strategies to overcome this resistance.

Elimusertib (BAY 1895344) hydrochloride is a potent, orally active and selective inhibitor of ataxia telangiectasia and RAD3-related (ATR) enzyme (Yap T A, Tan DSP, Terbuch A, Caldwell R, Guo C, Goh B C, Heong V, Haris N R M, Bashir S, Drew Y, Hong D S, Meric-Bernstam F, Wilkinson G, Hreiki J, Wengner A M, Bladt F, Schlicker A, Ludwig M, Zhou Y, Liu L, Bordia S, Plummer R, Lagkadinou E, de Bono J S. *First-in-Human Trial of the Oral Ataxia Telangiectasia and RAD*3-*Related* (*ATR*) *Inhibitor BAY* 1895344 *in Patients with Advanced Solid Tumors. Cancer Discov.* 2021 January; 11(1):80-91. doi: 10.1158 2159-8290.CD-20-0868. Epub 2020 Sep. 28). Elimusertib hydrochloride has anti-tumor activity and is currently investigated to the treatment of solid tumors and lymphomas. However, the interest of said compound in the treatment of pediatric liver cancers has never been investigated so far.

SUMMARY OF THE INVENTION

The present invention is defined by the claims. In particular the present relates to the combination of cisplatin and Elimusertib for the treatment of pediatric liver cancers.

DETAILED DESCRIPTION OF THE INVENTION

The first object of the present invention relates to a method of treating a pediatric liver cancer in a patient in need thereof comprising administering to the patient a therapeutically effective combination of cisplatin with elimusertib, wherein administration of the combination results in enhanced therapeutic efficacy relative to the administration of cisplatin alone.

In other words, the invention relates to a method of treating a pediatric liver cancer in a patient in need thereof comprising administering to the patient a therapeutically effective combination of cisplatin with elimusertib.

As used herein, the term "pediatric liver cancer" or "PLC" has its general meaning in the art and refers to a liver malignancy in children and adolescents and refers to different histological subgroups that include Hepatoblastoma, Hepatocellular Carcinoma, Malignant Rhabdoid Tumor (MRT), Undifferentiated Embryonal Sarcoma of Liver, Rhabdomyosarcoma of Liver, and Epithelioid hemangioendothelioma of the liver.

Thus, according to the present invention, the patient is a human child. In some embodiments, the patient is less than 15 years old. In some embodiments, the patient is less than 10 years old. In some embodiments, the patient is less than 7 years old. In some embodiments, the patient is less than 5 years old. In some embodiments, the patient is less than 3 years old.

In some embodiments, the pediatric liver cancer is hepatoblastoma. As used herein, the term "hepatoblastoma" has its general meaning in the art and refers to a pediatric liver cancer that arises from precursors of hepatocytes and can have several morphologies, including the following:

Small cells that reflect neither epithelial nor stromal differentiation. It is critical to discriminate between small cell undifferentiated hepatoblastoma expressing SMARCB1 and rhabdoid tumor of the liver, which lacks the SMARCB1 gene and SMARCB1 expression. Both diseases may share similar histology. Optimal treatment of rhabdoid tumor of the liver and small cell undifferentiated hepatoblastoma may require different approaches and different chemotherapy. (Refer to the Small cell undifferentiated histology hepatoblastoma and rhabdoid tumors of the liver section of this summary for a more extensive discussion of the differences between small cell undifferentiated hepatoblastoma and rhabdoid tumor of the liver.)

Embryonal epithelial cells resembling the liver epithelium at 6 to 8 weeks of gestation.

Well-differentiated fetal hepatocytes morphologically indistinguishable from normal fetal liver cells.

Most often the tumor consists of a mixture of epithelial hepatocyte precursors. About 20% of tumors have stromal derivatives such as osteoid, chondroid, and rhabdoid elements. Occasionally, neuronal, melanocytic, squamous, and enteroendocrine elements are found.

As used herein, the term "treatment" or "treat" refers to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

A further object of the present invention relates to a method for enhancing the therapeutic efficacy of cisplatin administered to a patient as part of a treatment regimen for a PLC, the method comprising administering a pharmaceutically effective amount of elimusertib to a patient in combination with cisplatin.

As used herein, the expression "enhancing therapeutic efficacy," relative to cancer refers to a slowing or diminution of the growth of cancer cells, or a reduction in the total number of cancer cells or total tumor burden. An "improved therapeutic outcome" or "enhanced therapeutic efficacy" therefore means there is an improvement in the condition of the patient according to any clinically acceptable criteria, including, for example, decreased tumor size, an increase in time to tumor progression, increased progression-free survival, increased overall survival time, an increase in life expectancy, a decrease of immune-adverse effects or an improvement in quality of life. In particular, "improved" or "enhanced" refers to an improvement or enhancement of 1%, 5%, 10%, 25% 50%, 75%, 100%, or greater than 100% of any clinically acceptable indicator of therapeutic outcome or efficacy. As used herein, the expression "relative to" when used in the context of comparing the activity and/or efficacy of a combination composition comprising cisplatin with elimusertib to the activity and/or efficacy of cisplatin alone, refers to a comparison using amounts known to be comparable according to one of skill in the art.

A further object of the present invention relates to a method of preventing relapse in patient suffering from a PLC after a treatment with cisplatin comprising administering to the patient a therapeutically effective amount of cisplatin in combination with elimusertib.

As used herein, the term "relapse" refers to reappearance of the cancer after an initial period of responsiveness (e.g., complete response or partial response). The initial period of responsiveness may involve the level of cancer cells falling below a certain threshold, e.g., below 20%, 15%, 10%, 5%, 4%, 3%, 2%, or 1%. The reappearance may involve the level of cancer cells rising above a certain threshold, e.g., above 20%, 15%, 10%, 5%, 4%, 3%, 2%, or 1%. More generally, a response (e.g., complete response or partial response) can involve the absence of detectable MRD (minimal residual disease). In some embodiments, the initial period of responsiveness lasts at least 1, 2, 3, 4, 6, 8, 10, or 12 months; or at least 1, 2, 3, 4, or 5 years.

A further object of the present invention relates to a method of preventing resistance to cisplatin therapy in a patient suffering from a PLC comprising administering to the patient a therapeutically effective amount of cisplatin in combination with elimusertib.

As used herein the term "resistance to cisplatin therapy" is used in its broadest context to refer to the reduced effectiveness of Cisplatin to inhibit the growth of a cell, kill a cell or inhibit one or more cellular functions, and to the ability of a cell to survive to an exposure to Cisplatin to inhibit the growth of the cell, kill the cell or inhibit one or more cellular functions. The resistance displayed by a cell may be acquired, for example by prior exposure to the agent, or may be inherent or innate. The resistance displayed by a cell may be complete in that the agent is rendered completely ineffective against the cell, or may be partial in that the effectiveness of the agent is reduced. Accordingly, the term "resistant" refers to the repeated outbreak of cancer, or a progression of cancer independently of whether the disease was cured before said outbreak or progression.

As used herein, the term "cisplatin" has its general meaning in the art and refers to cis-Diamminedichloroplatinum II that is an antineoplastic agent belonging to the family of platinum coordination complexes. It is a divalent inorganic water-soluble, platinum-containing complex.

As used herein, the term "elimusertib" has its general meaning in the art and refers to the compound having the general formula (I). The compound is also known as BAY-1895344. The Cas Number is 1876467-74-1. The IUAPC name is (3R)-3-methyl-4-[4-(2-methylpyrazol-3-yl)-8-(1H-pyrazol-5-yl)-1,7-naphthyridin-2-yl]morpholine.

(I)

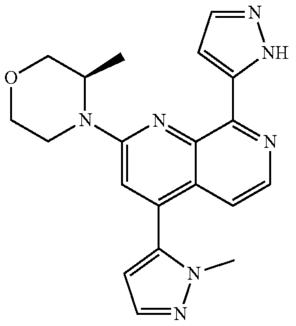

As used herein, the term "combination" is intended to refer to all forms of administration that provide a first drug together with a further (second, third . . . ) drug. The drugs may be administered simultaneous, separate or sequential and in any order. Drugs administered in combination have biological activity in the subject to which the drugs are delivered. Within the context of the invention, a combination thus comprises at least two different drugs, and wherein one drug is cisplatin and wherein the other drug is elimusertib.

In particular, the combination cisplatin with elimusertib results in the synthetic lethality of the cancer cells.

In particular, the combination of cisplatin with elimusertib results in synergistic effects as demonstrated in the EXAMPLE. As used herein, the term "synergistic effect" to action of two therapeutic agents such as, for example, (a) cisplatin, and (b) an elimusertib, producing an effect, for example, reducing the progression of the cancer, which is greater than the simple addition of the effects of each drug administered by themselves. A synergistic effect can be calculated using suitable methods such as described in the EXAMPLE. In particular, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. Synergy may be further shown by calculating the synergy score of the combination according to methods known by one of ordinary skill. The synergy can be assessed with the MacSynergy II (Prichard, M.N. and C. Shipman, Jr. 1990. A three-dimensional model to analyze drug-drug interactions. Antiviral Res. 14:181-206). This program allows the three-dimensional examination of drug interactions of all data points generated from the checkerboard combination of two inhibitors with Bliss-Independence model. Confidence bounds are determined from replicate data. If the 95% confidence limits (CL) do not overlap the theoretic additive surface, then the interaction between the two drugs differs significantly from additive. The volumes of synergy or antagonism can be determined and graphically depicted in three dimensions and represent the relative quantity of synergism or antagonism per change in the two drug concentrations. Synergy and antagonism volumes are based on the Bliss independence model, which assumes that both compounds act independently on different targets. A set of predicted fractional responses faAB under the Bliss independence model is calculated as $faAB=faA+faB-faA\cdot faB$ with faA and faB representing the fraction of possible responses, e.g. % inhibition, of compounds A and B at amounts dA and dB, respectively, and describes the % inhibition of a combination of compounds A and B at amount (dA+dB). If $faAB>faA+faB-faA\cdot faB$ then we have Bliss synergy; if $faAB<faA+faB-faA\cdot faB$ then we have Bliss antagonism. The 95% synergy/antagonism volumes are the summation of the differences between the observed inhibition and the 95% confidence limit on the prediction of faAB under the Bliss independence model.

As used herein, the expression "therapeutically effective amount" is meant a sufficient amount of the active ingredient (e.g. cisplatin or elimusertib) for treating or reducing the symptoms at reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination with the active ingredients; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, typically from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically, the drug of the present invention is administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a subject, the composition will be formulated for administration to the subject. The compositions of the present invention may be administered orally, parenterally, by inhalation spray, topically, rectally, nasally, buccally, vaginally or via an implanted reservoir. The used herein includes subcutaneous, intravenous, intramuscular, intra-articular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, an antibody present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/$m^2$ and 500 mg/$m^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of the inhibitor of the invention.

The invention will be further illustrated by the following figures and examples. However, these examples and figures should not be interpreted in any way as limiting the scope of the present invention.

FIGURES

FIG. 1: Sensitivity profiles of 22 drugs targeting DNA damage response alone and in combination with cisplatin in 9 pediatric liver cancer cell lines grown in monolayer. Each dot on the bar graphs represents one cell line. Combinations with cisplatin are shown as black bars and drugs alone are represented as white bars. Drugs are ranked according to their mean efficiency when combined with cisplatin across all the analyzed cell lines from the most effective combination (on the left, lowest GI50) to the less effective one (on the right, highest GI50).

Figure 2:
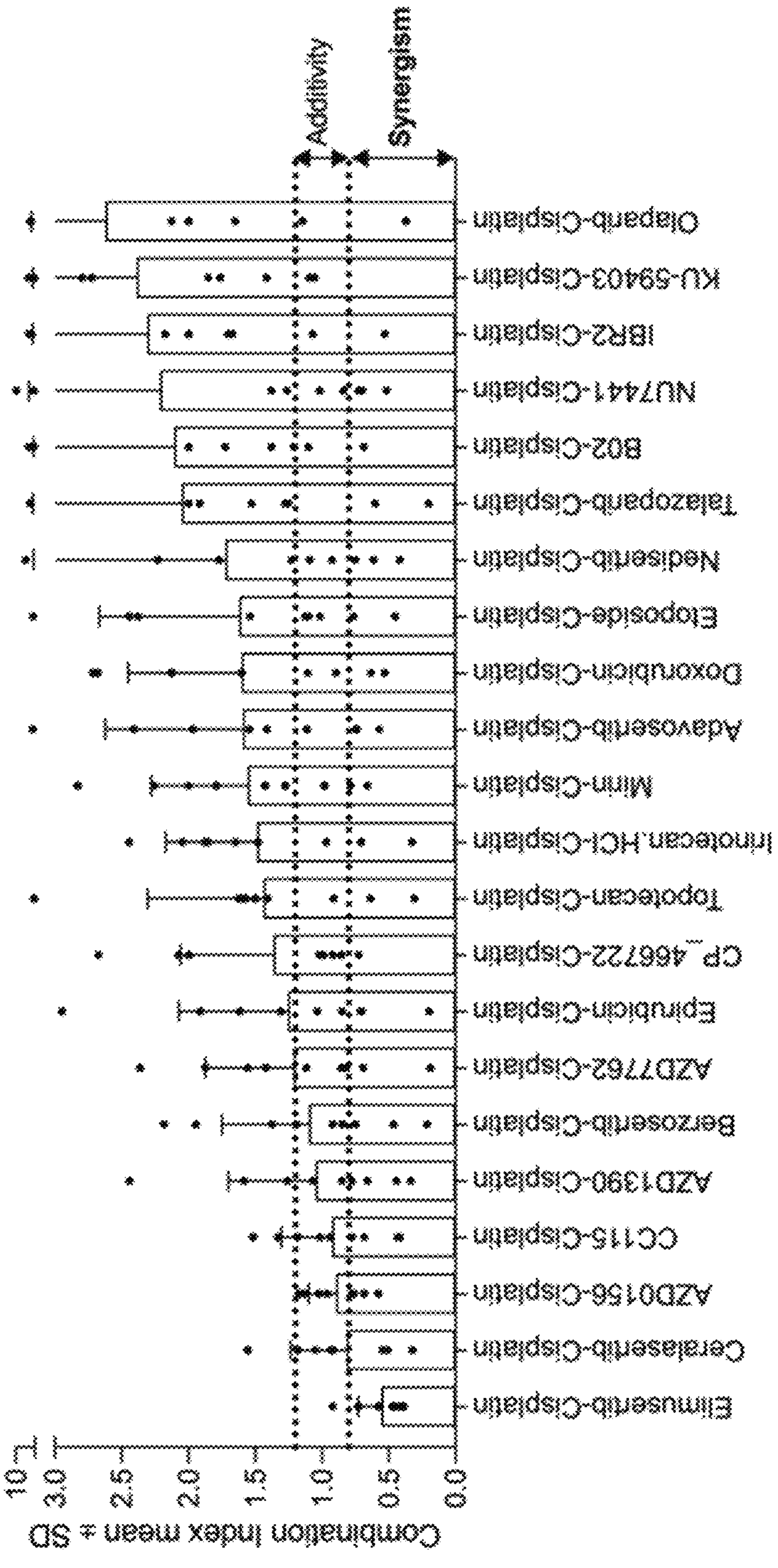
Figure 3A:
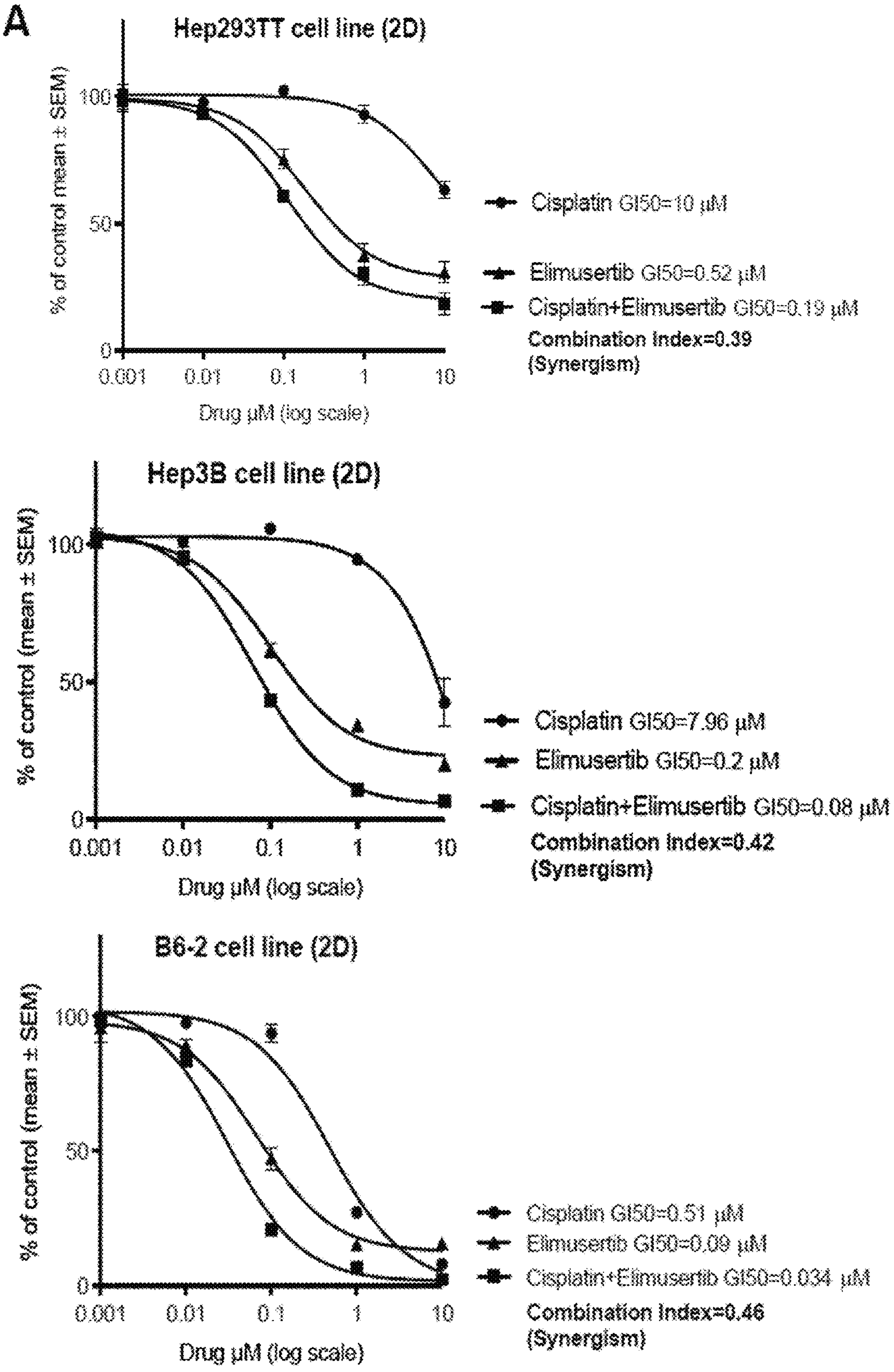
Figure 3A:
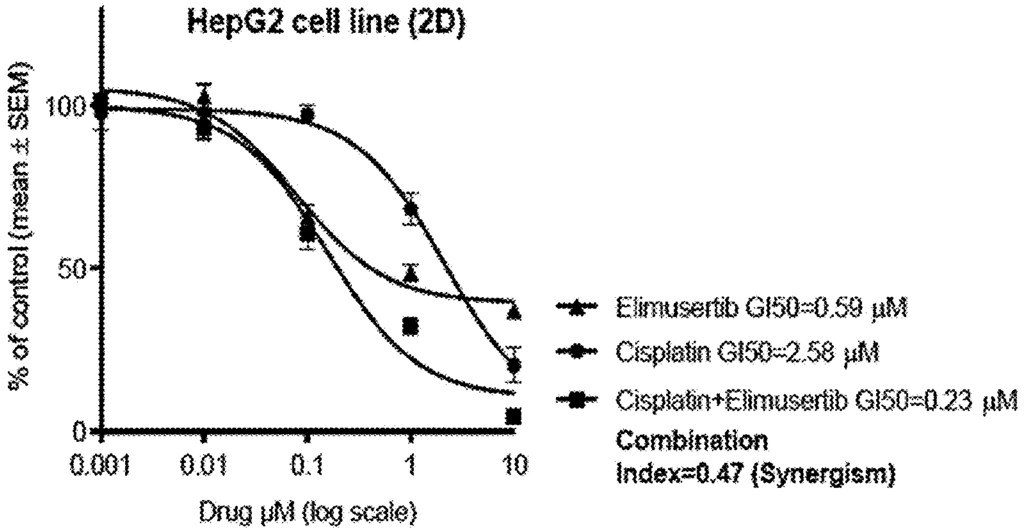
Figure 3A:
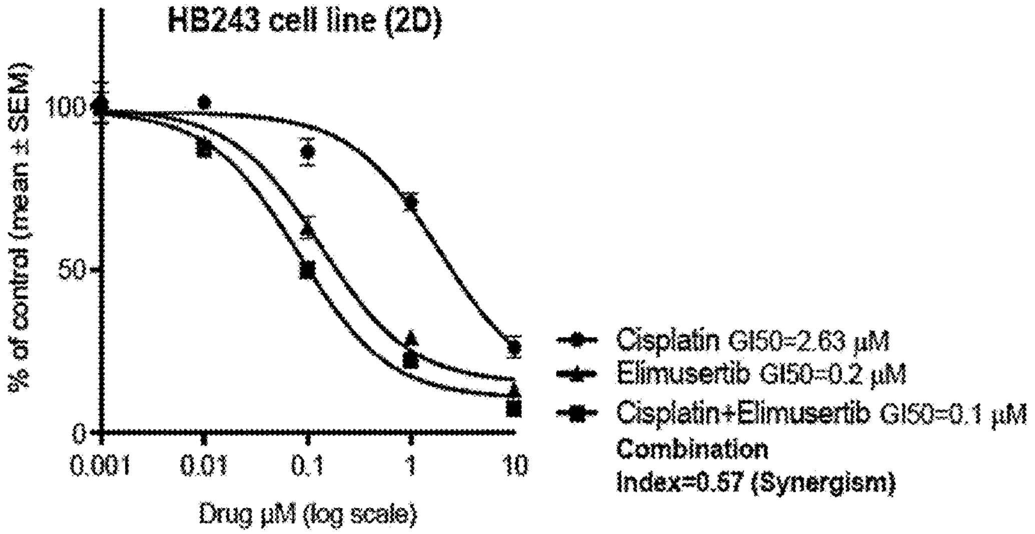
Figure 3A:
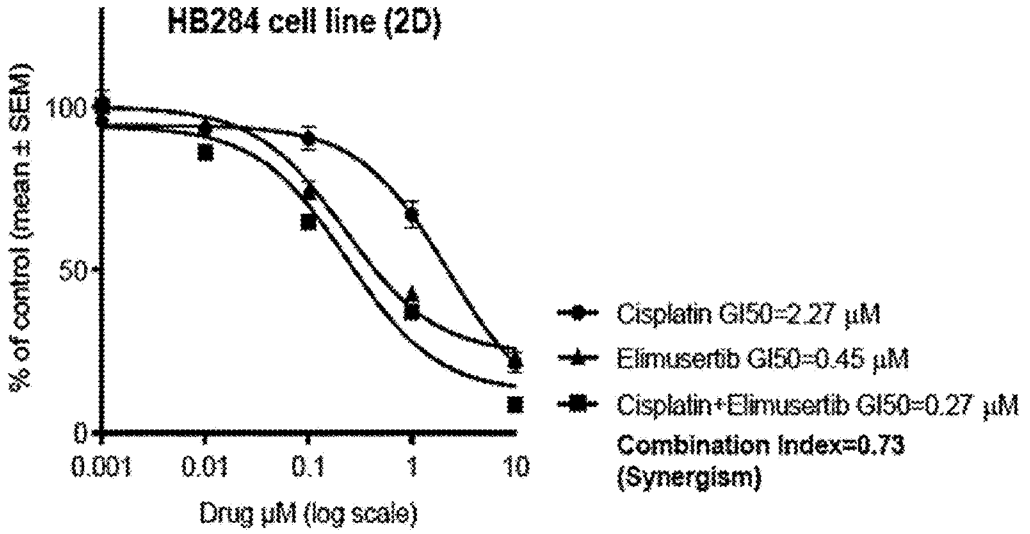
Figure 3A:
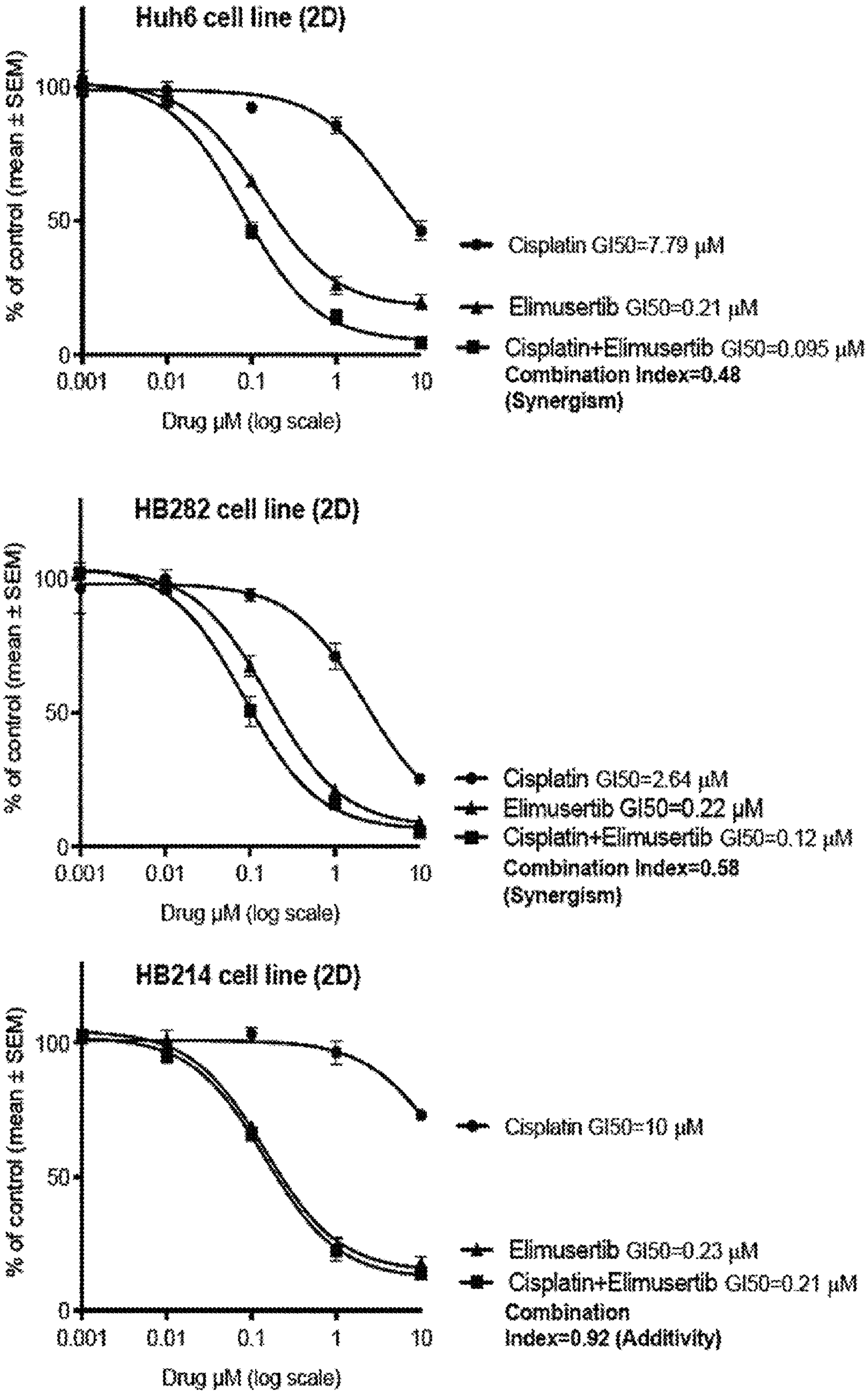
Figure 3B:
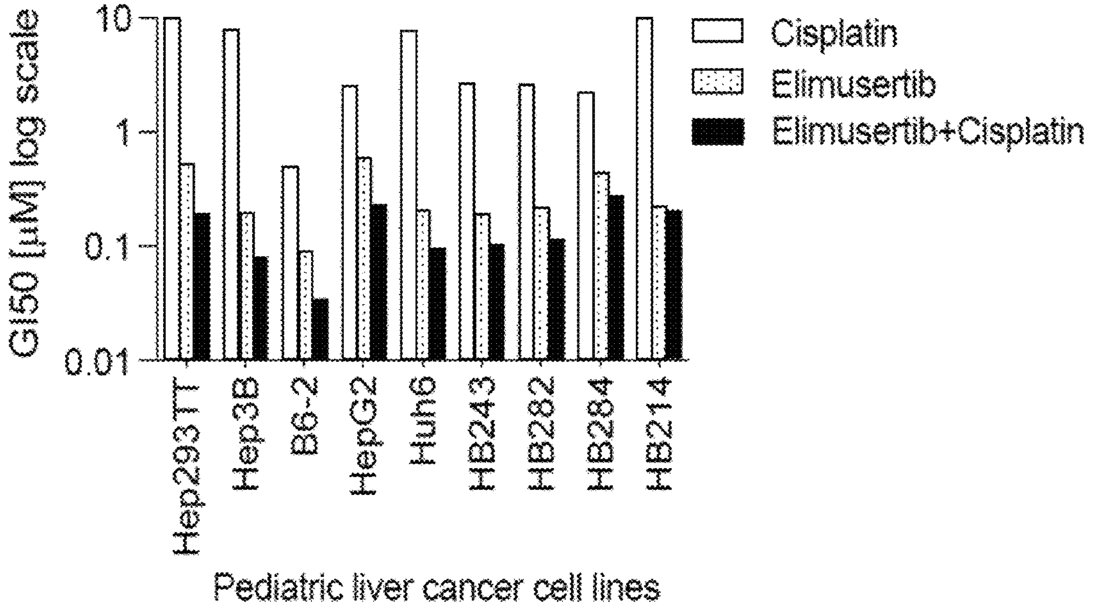
Figure 3C:
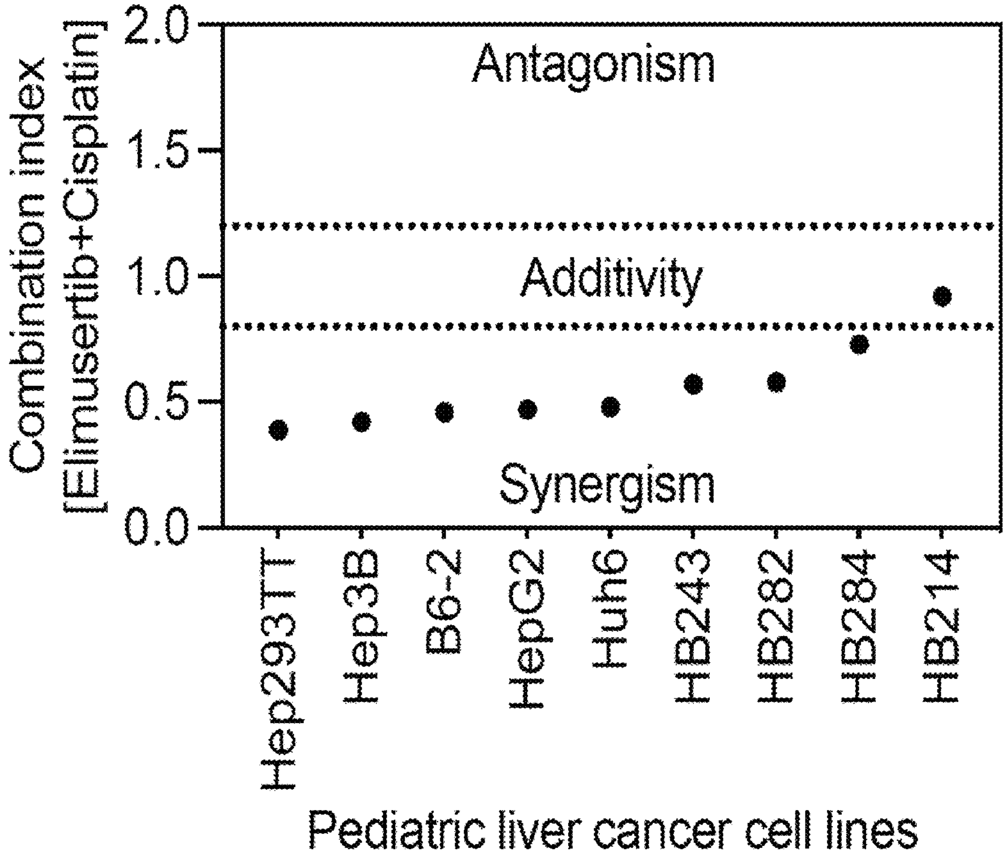
Figure 4A:
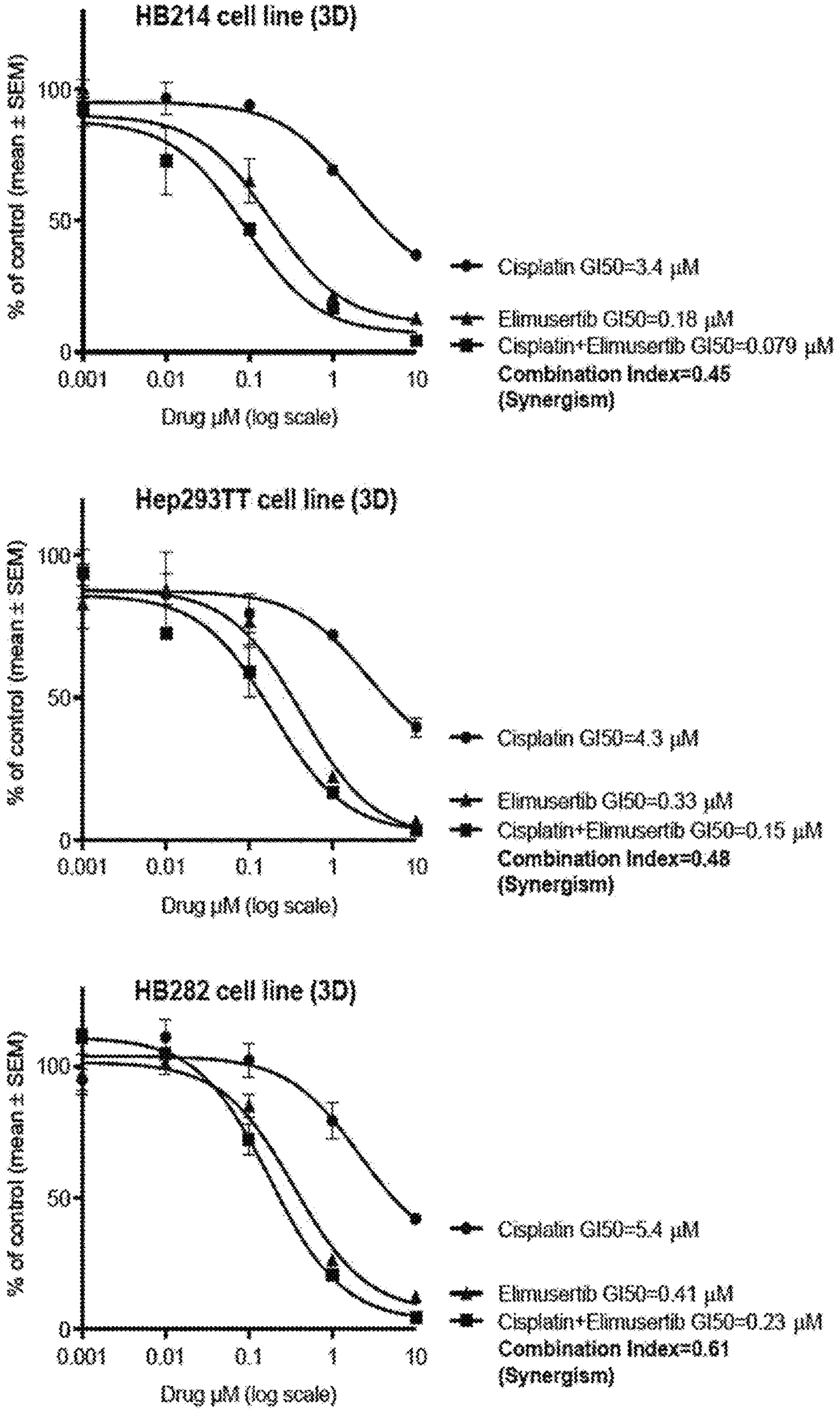
Figure 4A:
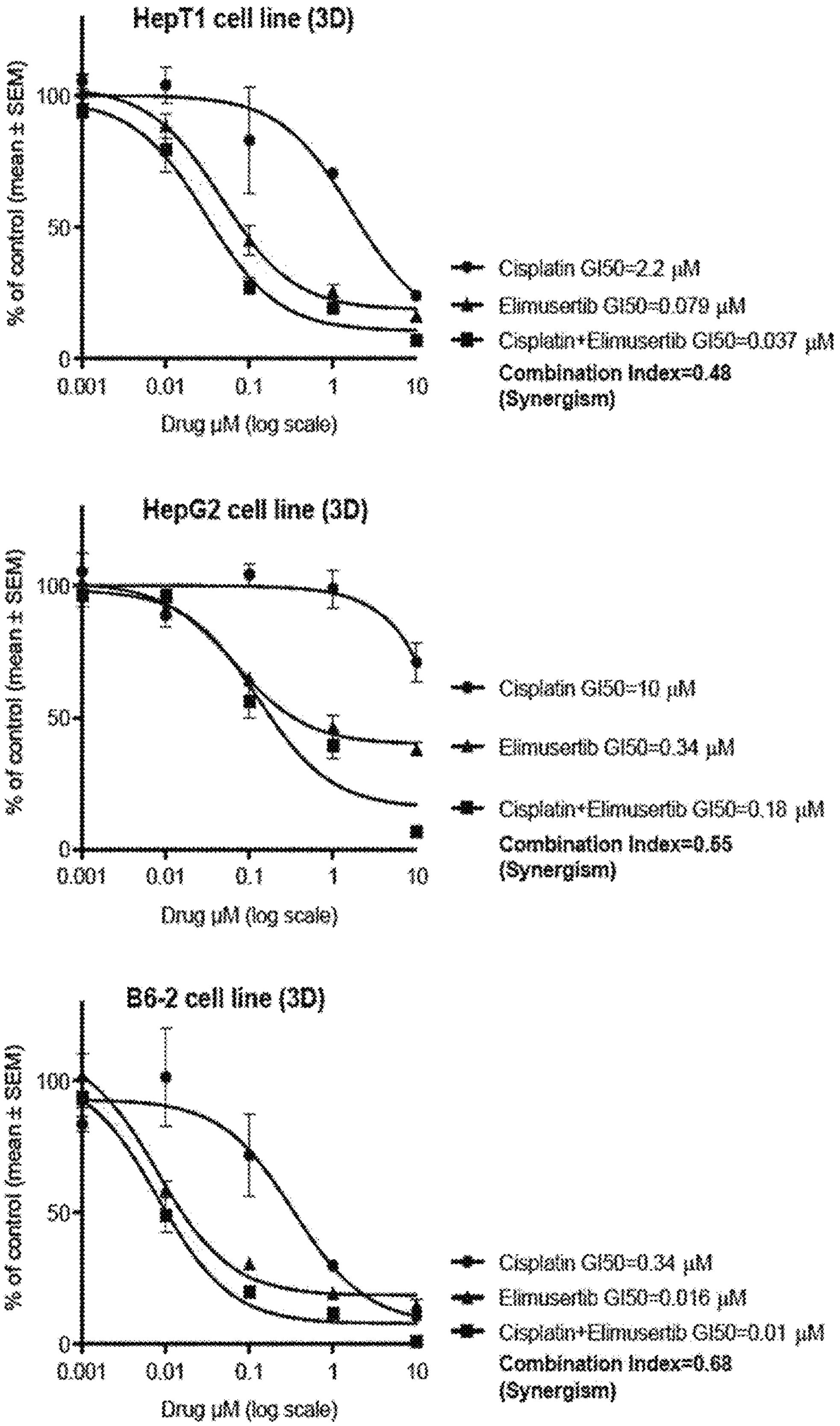
Figure 4A:
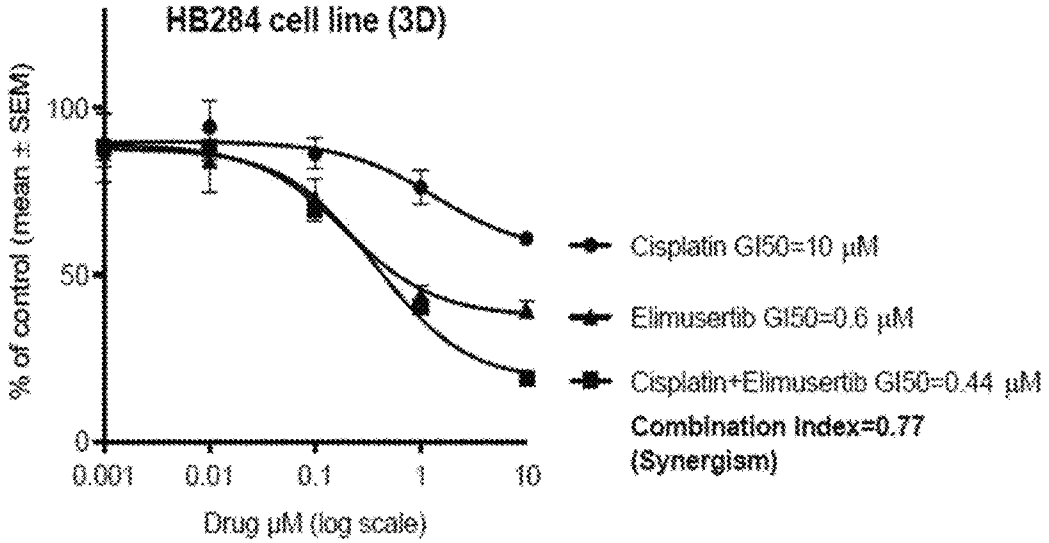
Figure 4B:
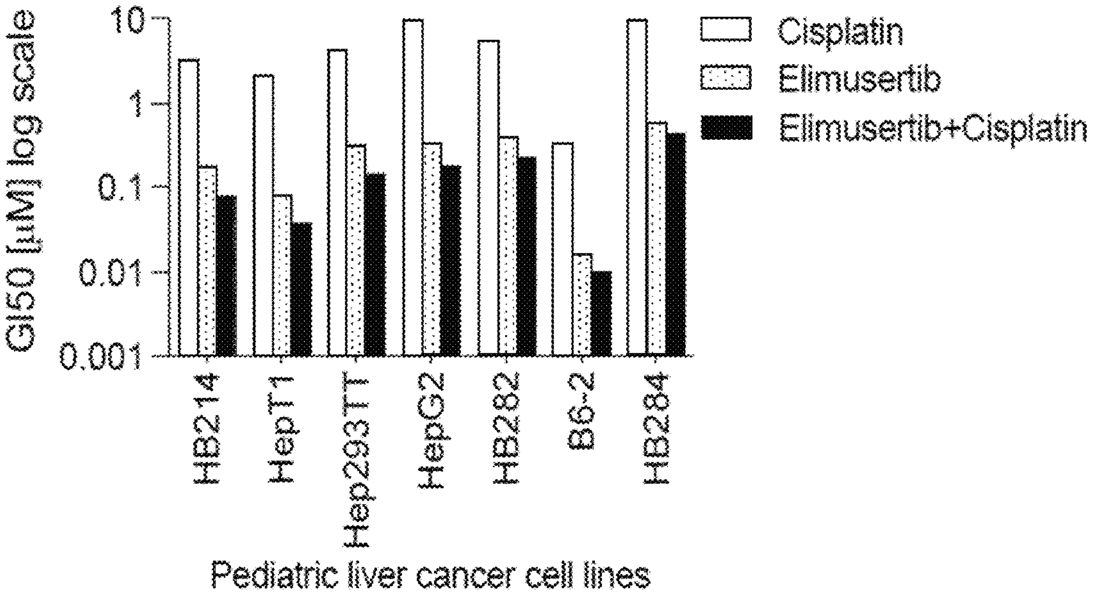
Figure 4C:
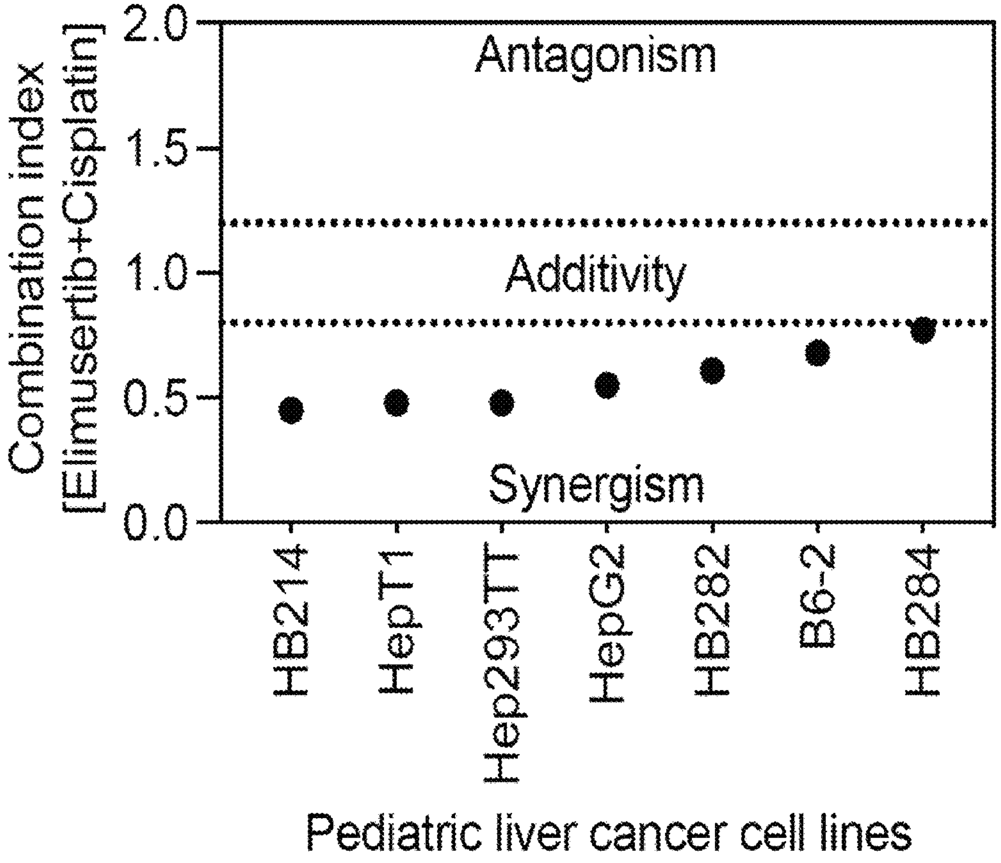

FIG. 2. Combination indexes for the 22 drugs targeting DNA damage response combined with cisplatin in 9 pediatric liver cancer cell lines grown in monolayer. Each dot on the bar graphs represents one cell line. Combinations are ranked according to the mean value of their combination index across all the analyzed cell lines from the lowest (most potent) to the highest (less potent). Combination index (CI) for each cell line and each drug combination was calculated with the equation of Chou and Talalay which defines synergistic (CI≤0.8), additive (0.8≤CI≤1.2) or antagonist (CI>1.2) interaction between the two compounds.

FIG. 3. Elimusertib and Cisplatin combination shows synergistic efficacy on tumor cell viability inhibition in pediatric liver cancer cell lines grown in monolayer. A. Dose-response curves showing sensitivity to Cisplatin and Elimusertib alone and in combination for 9-pediatric liver cancer cell lines (8 derived from hepatoblastoma and 1 from a pediatric hepatocellular carcinoma). Cell viability was determined after 72 h of drug exposure using the MTS assay. For each cell line and each compound, the GI50 (the concentration that reduces of 50% the viability of treated cells) is shown and the combination index was calculated with the equation of Chou and Talalay. B. Summary of sensitivity profiles assessed by the GI50 for Elimusertib and Cisplatin alone and in combination for the 9-pediatric liver cancer cell lines analyzed. C. Summary of combination index values at GI50 for Elimusertib and Cisplatin treatment showing synergism in 8 of the 9-pediatric liver cancer cell lines analyzed.

FIG. 4. Elimusertib and Cisplatin combination shows synergistic efficacy on tumor cell viability inhibition in pediatric liver cancer cell lines grown in 3-dimensions. A. Dose-response curves showing sensitivity to Cisplatin and Elimusertib alone and in combination for 7-pediatric liver cancer cell lines (all hepatoblastoma). Cell viability was determined after 72 h of drug exposure using the CellTiter-Glo 3D assay. For each cell line and each compound, the GI50 (the concentration that reduces of 50% the viability of treated cells) is shown and the combination index was calculated with the equation of Chou and Talalay. B. Summary of sensitivity profiles assessed by the GI50 for Elimusertib and Cisplatin alone and in combination for the 7-pediatric liver cancer cell lines analyzed. C. Summary of combination index values at GI50 for Elimusertib and Cisplatin treatment showing synergism in the 7-pediatric liver cancer cell lines analyzed.

TABLES

TABLE 1

Description of the collection of pediatric liver cancer cell lines.

| Cell line ID | Cellosaurus ID | Supplier | Reference | Diag- nosis | Age | Gen- der | Type of tumor from which the cell line is derived | Culture Medium |
|---|---|---|---|---|---|---|---|---|
| HepG2 | CVCL_0027 | ATCC - USA | Aden et al. Nature (1979) | HB | 15 | Male | Primary tumor (biopsy) | DMEM, high glucose pyruvate (#41966-052, Thermo Fisher Scientific), 10% FBS, 1% penicillin/streptomycin |
| Huh6 | CVCL_4381 | RIKEN BioResource Center - Japan | Doi et al. Gan (1976) | HB | 1 | Male | NA | DMEM, high glucose pyruvate (#41966-052, Thermo Fisher Scientific), 10% FBS, 1% penicillin/streptomycin |
| Hep293TT | CVCL_D139 | Gift from Xin Chen, USCF - USA | Chen et al. Pediatr Blood Cancer (2009) | HB | 5 | Female | NA | DMEM, high glucose pyruvate (#41966-052, Thermo Fisher Scientific), 10% FBS, 1% penicillin/streptomycin |
| B6-2 | NA | Gift from Karl-Dimiter Bissig, Baylor College - USA | Bissig-Choisat et al. J Hepatol. (2016) | HB | 7 | Male | NA | DMEM, high glucose pyruvate (#41966-052, Thermo Fisher Scientific), 10% FBS, 1% penicillin/streptomycin |
| HepT1 | CVCL_G003 | Gift from Karl-Dimiter Bissig, Baylor College - USA | Pietsch et al. Lab Invest. (1996) | HB | 3 | Female | Primary tumor | DMEM, high glucose pyruvate (#41966-052, Thermo Fisher Scientific), 10% FBS, 1% penicillin/streptomycin |
| HB214 | NA | XenTech - France | Nicolle et al. Hepatology (2016) Cell line derived from PDTX | HB | NA | Female | NA | Advanced DMEM F12 (#12634028, Thermo Fisher Scientific), 10% FBS, 1% penicillin/streptomycin |
| HB243 | NA | XenTech - France | Nicolle et al. Hepatology (2016) Cell line derived from PDTX | HB | 3 | Male | Local relapse | Advanced DMEM F12 (#12634028, Thermo Fisher Scientific), 10% FBS, 1% penicillin/ streptomycin + 20 µM ROCK inhibitor |
| HB284 | NA | XenTech - France | Nicolle et al. Hepatology (2016) Cell line derived from PDTX | HB | 6.5 | Male | Relapse (metastasis) | Advanced DMEM F12 (#12634028, Thermo Fisher Scientific), 10% FBS, 1% penicillin/ streptomycin + 20 µM ROCK inhibitor |
| HB282 | NA | XenTech - France | Nicolle et al. Hepatology (2016) Cell line derived from PDTX | HB | 1 | Male | Primary tumor | Advanced DMEM F12 (#12634028, Thermo Fisher Scientific), 10% FBS, 1% penicillin/streptomycin + 20 µM ROCK inhibitor |
| Hep3B | CVCL_0326 | ATCC - USA | Aden et al. Nature (1979) | HCC | 8 | Male | Primary tumor | DMEM, high glucose pyruvate (#41966-052, Thermo Fisher Scientific), 10% FBS, 1% penicillin/streptomycin |

HB: hepatoblastoma,
HCC: hepatocellular carcinoma,
NA: not available

TABLE 2

Description of the pharmacological compounds analyzed.

| Drug name (alias) | Target | Clinical status in any tumor type | Clinical status in pediatric liver cancer (HB) | Supplier | Reference |
|---|---|---|---|---|---|
| Adavosertib (MK-1775) | WEE1 | Phase 1/2 (Childhood), Phase 2 (Adult) | None | Selleck Chemicals | S1525 |
| AZD0156 | ATM | Phase 1 (Adult) | None | Selleck Chemicals | S8375 |
| AZD1390 | ATM | Phase 1 (Adult) | None | Selleck Chemicals | S8680 |
| AZD7762 | CHK1 | Phase 1 (Adult) | None | Selleck Chemicals | S1532 |
| B02 | RAD51 | None | None | Selleck Chemicals | S8434 |
| Elimusertib (BAY-1895344) | ATR | Phase 1/2 (Childhood), Phase 1 (Adult) | None | TargetMol | T7318 |
| Berzosertib (VX-970) | ATR | Phase 2 (Childhood), Phase 2 (Adult) | None | Selleck Chemicals | S7102 |

TABLE 2-continued

Description of the pharmacological compounds analyzed.

| Drug name (alias) | Target | Clinical status in any tumor type | Clinical status in pediatric liver cancer (HB) | Supplier | Reference |
|---|---|---|---|---|---|
| CC115 | DNA-PK and mTOR | Phase 1 (Adult) | None | Selleck Chemicals | S7891 |
| Ceralasertib (AZD6738) | ATR | Phase 2 (Childhood), Phase 3 (Adult) | None | Selleck Chemicals | S7693 |
| CP_466722 | ATM | None | None | Selleck Chemicals | S2245 |
| Doxorubicin (Adriamycin) | TOP2A/ TOP2B | Approved (Childhood and Adult) | Approved (standard of care) | Selleck Chemicals | S1208 |
| Epirubicin (IMI 28) | TOP2A/ TOP2B | Approved (Childhood and Adult) | None | Selleck Chemicals | S1223 |
| Etoposide (VP-16) | TOP2A/ TOP2B | Approved (Childhood and Adult) | Approved | Selleck Chemicals | S1225 |
| IBR2 | RAD51 | None | None | MedChemExpress | HY-103710 |
| Irinotecan_HCl (CPT-11) | TOP1 | Approved (Childhood and Adult) | Approved | Selleck Chemicals | S2217 |
| KU-59403 | ATM | None | None | MedChemExpress | HY-18650 |
| Mirin | MRE11 | None | None | Selleck Chemicals | S8096 |
| Nedisertib (M3814) | DNA-PK | Phase 1 (Adult) | None | MedChemExpress | HY-101570 |
| NU7441 (KU-57788) | DNA-PK | None | None | Selleck Chemicals | S2638 |
| Olaparib (AZD2281) | PARP1/2 | Phase 2 (Childhood), approved (Adult) | Phase 2 | Selleck Chemicals | S1060 |
| Talazoparib (BMN 673) | PARP1/2 | Phase 2 (Childhood), approved (Adult) | Phase 2 | Selleck Chemicals | S7048 |
| Topotecan | TOP1 | Phase 3 (Childhood), approved (Adult) | Phase 2 | Selleck Chemicals | S1231 |
| Cisplatin | DNA crosslinker | Approved (Childhood and Adult) | Approved (standard of care) | Selleck Chemicals | S1166 |

(HB): hepatoblastoma

TABLE 3

Potency of the 22 compounds targeting DNA damage response combined with cisplatin in 9 pediatric liver cancer cell lines grown in monolayer.

| | | Combination efficiency | | | | Combination index (CI) | | | | | | |
|---|---|---|---|---|---|---|---|---|---|---|---|---|
| Drug combinations | Target of the first compound | Mean GI50 (μM) | Median GI50 (μM) | SD GI50 (μM) | Combination efficiency rank | Mean (CI) | Median (CI) | SD (CI) | % of synergism | % of additivity | CI rank | Final rank |
| Elimusertib-Cisplatin | ATR | 0.15 | 0.12 | 0.08 | 3 | 0.56 | 0.48 | 0.17 | 88.9 | 11.1 | 1 | 4 |
| CC115-Cisplatin | DNA-PK | 0.33 | 0.35 | 0.14 | 5 | 0.92 | 0.94 | 0.38 | 44.4 | 33.3 | 4 | 9 |
| Epirubicin-Cisplatin | TOP2A/TOP2B | 0.09 | 0.09 | 0.06 | 1 | 1.26 | 1.04 | 0.82 | 33.3 | 22.2 | 8 | 9 |
| Ceralasertib-Cisplatin | ATR | 1.45 | 1.91 | 0.75 | 10 | 0.82 | 0.92 | 0.42 | 44.4 | 44.4 | 2 | 12 |
| AZD0156-Cisplatin | ATM | 1.15 | 1.11 | 0.44 | 9 | 0.90 | 0.96 | 0.20 | 44.4 | 55.6 | 3 | 12 |
| Berzosertib-Cisplatin | ATR | 0.59 | 0.39 | 0.38 | 7 | 1.10 | 0.92 | 0.65 | 33.3 | 33.3 | 6 | 13 |
| AZD7762-Cisplatin | CHK1 | 0.55 | 0.41 | 0.39 | 6 | 1.21 | 1.12 | 0.66 | 22.2 | 33.3 | 7 | 13 |
| Topotecan-Cisplatin | TOP1 | 0.30 | 0.18 | 0.29 | 4 | 1.44 | 1.50 | 0.87 | 22.2 | 11.1 | 10 | 14 |
| Doxorubicin-Cisplatin | TOP2A/TOP2B | 0.12 | 0.13 | 0.06 | 2 | 1.60 | 1.60 | 0.85 | 22.2 | 22.2 | 4 | 16 |
| AZD1390-Cisplatin | ATM | 3.22 | 3.06 | 2.50 | 14 | 1.05 | 0.85 | 0.65 | 44.4 | 22.2 | 5 | 19 |
| CP_466722-Cisplatin | ATM | 2.58 | 2.81 | 1.25 | 12 | 1.36 | 0.99 | 0.70 | 11.1 | 55.6 | 9 | 21 |
| Adavosertib-Cisplatin | WEE1 | 0.77 | 0.65 | 0.53 | 8 | 1.59 | 1.41 | 1.03 | 33.3 | 11.1 | 13 | 21 |
| Irinotecan•HCl-Cisplatin | TOP1 | 3.38 | 2.70 | 2.63 | 15 | 1.49 | 1.65 | 0.69 | 22.2 | 11.1 | 11 | 26 |
| Etoposide-Cisplatin | TOP2A/TOP2B | 2.42 | 1.89 | 2.40 | 11 | 1.62 | 1.13 | 1.05 | 22.2 | 33.3 | 15 | 26 |
| Mirin-Cisplatin | MRE11 | 4.79 | 3.95 | 3.25 | 17 | 1.56 | 1.43 | 0.72 | 22.2 | 11.1 | 12 | 29 |
| Nedisertib-Cisplatin | DNA-PK | 3.56 | 2.41 | 3.14 | 16 | 1.73 | 1.10 | 1.87 | 33.3 | 22.2 | 16 | 32 |
| NU7441-Cisplatin | DNA-PK | 2.71 | 1.74 | 2.80 | 13 | 2.21 | 1.02 | 3.04 | 33.3 | 22.2 | 19 | 32 |
| Talazoparib-Cisplatin | PARP | 6.04 | 6.79 | 4.10 | 19 | 2.05 | 1.53 | 1.68 | 22.2 | 0.0 | 17 | 36 |
| B02-Cisplati | RAD51 | 6.06 | 6.05 | 3.55 | 20 | 2.11 | 1.73 | 1.47 | 11.1 | 11.1 | 18 | 38 |
| KU-59403-Cisplatin | ATM | 5.37 | 5.75 | 2.70 | 18 | 2.39 | 1.85 | 1.39 | 0.0 | 22.2 | 21 | 39 |
| IBR2-Cisplatin | RAD51 | 6.86 | 8.69 | 3.82 | 21 | 4.31 | 2.00 | 1.54 | 11.1 | 11.1 | 20 | 41 |
| Olaparib-Cisplatin | PARP | 7.40 | 9.32 | 3.63 | 22 | 2.62 | 2.00 | 1.70 | 11.1 | 11.1 | 22 | 44 |

Potency of each drug combination was evaluated by taking into account both its efficiency defined by the GI50 and its combination index defining the nature of the interaction between the two compounds as synergistic (CI≤0.8), additive (0.8≤CI≤1.2) or antagonist (CI>1.2). % of synergism or additivity define the percentage of cell lines with a synergistic or an additive interaction for a given combination. Combinations were first ranked independently according to their mean GI50 and CI from the lowest (rank 1) to the highest (rank 22), then the final rank was calculated as the sum of the "combination efficiency rank" and "the CI rank". Combinations are classified according to their final rank highlighting Elimusertib-Cisplatin combination as the most potent one. CI: combination index, SD: standard deviation.

EXAMPLE

Methods

Pediatric Liver Cancer Cell Lines

A panel of 10 pediatric liver cancer cell lines was collected from public repositories, academic collaborators and from a private company (XenTech) (Table 1). Cells were grown at 37° C., 5% $CO_2$ in either DMEM or Advanced DMEM F-12 supplemented with 10% fetal bovine serum, 100 U/mL penicillin/streptomycin and 1% glutamine (Thermo Fisher Scientific), in presence of ROCK inhibitor (Y-27632 20 μM, StemCell Technologies) for 3 cell lines (Table 1). Cell line identity was confirmed using whole-exome sequencing. The absence of *mycoplasma* contamination was confirm using MycoAlert *Mycoplasma* PLUS detection kit (Lonza).

Spheroid Formation

The "BioPearl" technology developed and patented by Cyprio (France) was used for spheroid formation for 7 pediatric liver cancer cell lines. Tumor cells were encapsulated in alginate microcapsules uniform in size measuring an average of 400 μm in diameter. Briefly, a homemade coextrusion device (Alessandri, PNAS 2013 PMID: 23980147; Domejean, Lab on Chip 2017 PMID: 27869911) was used to produce two-layer micrometric droplets with the shell based on 1.7% wt sodium alginate solution (Sodium Alginate Protanal LF200 FTS, FMC Corporation) with 0.5 mM of Sodium Dodecyl Sulfate (Sigma-Aldrich) and the core being a mixture of suspended tumor cells (6 or 7 million cells/ml corresponding to 130 or 150 cells/capsule, depending on the cell line) and 2-Hydroxyethyl Cellulose (HEC) (Sigma-Aldrich) with culture medium solution. After the physical crosslinking of the outer layer inside a calcium bath (100 mM calcium chloride and traces of Tween 20, Sigma-Aldrich), tumor cells were trapped inside porous hydrogel capsules allowing the flow of the essential nutrients. These capsules were produced at a rate of 1200 capsules per second and collected for tens of seconds. After washing the microcapsules in the appropriate culture medium, they were cultivated, and the medium was changed every twice a week.

Pharmacological Compounds 22 pharmacological compounds targeting various protein involved in DNA damage response were analyzed alone and in combination with cisplatin (Table 2). Cisplatin (S1166, Selleck Chemicals) was dissolved in $H_2O$, 0.9% NaCl, 0.3% Tween20 at a 0.5 g/L final concentration and the 22 other compounds were dissolved in DMSO at 10 mM final concentration.

Drug Testing and Viability Assays

Drug sensitivity profiles were evaluated in 2-dimensional and 3-dimensional cell culture. Drugs were distributed using the HP D300 digital dispenser (Tecan) that enables automated delivery of picoliter volumes of small molecule compounds to create dose-response curves. Cells were seeded in 96-well plates at an optimal density previously determined (2500 to 5000 cells/well for 2D experiments and 130 to 150 cells/microcapsule and 10 microcapsules/well for 3D experiments) to ensure that vehicle-treated cells were in growth phase at the end of the experiment. Tumor cell lines were grown in the appropriate culture medium (see Table 1). Cells were then treated for 72 hours with 5 concentrations of each compound (10-fold dilution from 0.001 to 10 μM and a non-treated negative control in duplicates in at least two independent experiments for 2D cell culture, in triplicates in one experiment for 3D cell culture). For combinations, drugs were combined at a constant concentration ratio (1:1) as recommended in the method of Chou and Talalay (Chou T-C Cancer Res 2010 PMID: 20068163) using the same range of concentration as described above.

After medium removal cells grown in 2D were incubated with MTS solution (CellTiter 96® AQueous One Solution Cell Proliferation Assay, Promega) diluted 1:6 in fresh culture medium and viability was assessed by recording absorbance at 490 nm using the FLUOstar Omega microplate reader (BMG Labtech).

For 3D culture, an equivalent volume of CellTiter-Glo® 3D Reagent (Promega) was added, plate was shaken for 5 minutes, all samples were then transferred to a 96-well standard white assay plate (#136102 Thermo Scientific) and viability was assessed by recording luminescence 30 minutes after reagent addition using the FLUOstar Omega microplate reader (BMG Labtech).

Standard of References for Analysis of Drug Sensitivity in Cellulo

Curve fitting of dose-response data were performed using GraphPad Prism 7 Software to determine the GI50 corresponding to the concentration of drug that inhibits 50% of cell viability. When the GI50 was not reached, the values were set to the highest concentration tested (10 μM). For combinations, the nature of drug interaction was defined from the dose-response curves at GI50 using the Combination Index (CI) equation developed by Chou and Talalay (Chou T-C Cancer Res 2010 PMID: 20068163):

$$CI = \frac{GI50_{drug1+2}}{GI50_{drug1}} + \frac{GI50_{drug1+2}}{GI50_{drug2}}$$

The CI value provides a quantitative estimation of drug interaction indicating synergistic (CI≤50.8), additive (0.8≤CI≤1.2) or antagonist (CI>1.2) effects.

Results

We analysed the combination of 22 drugs targeting DNA damage responses with cisplatin in pediatric liver cancer lines (FIG. 1, Table 2). Only the combination of Elimusertib and cisplatin shows a potent synergistic efficacy (Table 3 and FIG. 2). The results are depicted in FIGS. 1, 2, 3 and 4 and demonstrate synergistic efficacy of the combination of Elimusertib and Cisplatin on tumor cell viability inhibition in pediatric liver cancer cell lines.

REFERENCES

Throughout this application, various references describe the state of the art to which this invention pertains. The disclosures of these references are hereby incorporated by reference into the present disclosure.

The invention claimed is:

1. A method of treating a pediatric liver cancer (PLC) in a patient in need thereof and/or for enhancing the therapeutic efficacy of cisplatin administered to the patient as part of a treatment regimen for the PLC comprising administering to the patient a therapeutically effective combination of cisplatin with elimusertib, wherein administration of the combination results in enhanced therapeutic efficacy relative to the administration of cisplatin alone.

2. A method of preventing relapse in patient suffering from a pediatric liver cancer (PLC) after a treatment with cisplatin comprising administering to the patient a therapeutically effective amount of cisplatin in combination with elimusertib.

3. A method of preventing resistance to cisplatin therapy in a patient suffering from a pediatric liver cancer (PLC) comprising administering to the patient a therapeutically effective amount of cisplatin in combination with elimusertib.

4. The method of claim 1 wherein the patient is less than 15 years old, or the patient is less than 10 years old, or the patient is less than 7 years old, or the patient is less than 5 years old or the patient is less than 3 years old.

5. The method of claim 1 wherein the pediatric liver cancer is hepatoblastoma.

6. The method of claim 2, wherein the patient is less than 15 years old, or the patient is less than 10 years old, or the patient is less than 7 years old, or the patient is less than 5 years old or the patient is less than 3 years old.

7. The method of claim 2, wherein the pediatric liver cancer is hepatoblastoma.

8. The method of claim 3, wherein the patient is less than 15 years old, or the patient is less than 10 years old, or the patient is less than 7 years old, or the patient is less than 5 years old or the patient is less than 3 years old.

9. The method of claim 3, wherein the pediatric liver cancer is hepatoblastoma.

* * * * *